United States Patent
Marchesini et al.

(10) Patent No.: US 10,874,872 B2
(45) Date of Patent: Dec. 29, 2020

(54) LASER THERAPY APPARATUS

(71) Applicant: ASA S.R.L., Arcugnano (IT)

(72) Inventors: Roberto Marchesini, Schio (IT); Lucio Zaghetto, Castelfranco Veneto (IT)

(73) Assignee: ASA S.R.L., Arcugnano (IT)

( * ) Notice: Subject to any disclaimer, the term of this patent is extended or adjusted under 35 U.S.C. 154(b) by 184 days.

(21) Appl. No.: 16/118,016

(22) Filed: Aug. 30, 2018

(65) Prior Publication Data
US 2019/0070429 A1 Mar. 7, 2019

(30) Foreign Application Priority Data
Sep. 4, 2017 (IT) .................. 102017000098576

(51) Int. Cl.
| | |
|---|---|
| *A61N 5/06* | (2006.01) |
| *A61B 18/22* | (2006.01) |
| *G02B 6/42* | (2006.01) |
| *H01S 5/022* | (2006.01) |
| *H01S 5/40* | (2006.01) |
| *H01S 5/00* | (2006.01) |
| *A61B 17/00* | (2006.01) |
| *A61N 5/067* | (2006.01) |

(52) U.S. Cl.
CPC .............. *A61N 5/06* (2013.01); *A61B 18/22* (2013.01); *G02B 6/425* (2013.01); *A61B 2017/00154* (2013.01); *A61B 2018/2211* (2013.01); *A61N 2005/063* (2013.01); *A61N 2005/067* (2013.01); *A61N 2005/0651* (2013.01); *G02B 6/4292* (2013.01); *H01S 5/005* (2013.01); *H01S 5/02284* (2013.01); *H01S 5/4087* (2013.01)

(58) Field of Classification Search
CPC .............. A61N 5/06; A61N 2005/063; A61N 2005/0651; A61N 2005/067; A61B 18/22; A61B 2018/2211; A61B 2017/00154; G02B 6/425; G02B 6/4292; H01S 5/02284; H01S 5/4087; H01S 5/005
See application file for complete search history.

(56) References Cited

U.S. PATENT DOCUMENTS

| | | | |
|---|---|---|---|
| 5,172,264 A | 12/1992 | Morrow | |
| 2006/0153254 A1 | 7/2006 | Franjic et al. | |
| 2011/0167656 A1* | 7/2011 | Huang | H01S 5/005 33/286 |
| 2011/0237999 A1* | 9/2011 | Muller | A61B 3/107 604/20 |
| 2014/0113243 A1* | 4/2014 | Boutoussov | A61C 1/081 433/29 |
| 2015/0273236 A1* | 10/2015 | Rogers | A61N 5/0601 607/80 |
| 2016/0135892 A1* | 5/2016 | Yu | A61B 18/20 606/3 |
| 2016/0192988 A1* | 7/2016 | Albright | A61B 18/22 606/11 |

FOREIGN PATENT DOCUMENTS

WO 9514251 A1 5/1995

\* cited by examiner

*Primary Examiner* — Scott M. Getzow
(74) *Attorney, Agent, or Firm* — Cantor Colburn LLP

(57) ABSTRACT

A laser therapy apparatus having a diode-based continuous emission laser source, a diode-based pulsed emission laser source, and a terminal handpiece. The laser therapy apparatus further includes a bundle of optic fibers for coupling between individual diodes of the diode-based pulsed emission laser source, which is interfaced with a single optic fiber which terminates in the handpiece.

12 Claims, 3 Drawing Sheets

LASER THERAPY APPARATUS

CROSS-REFERENCE TO RELATED APPLICATIONS

This application is related to, and claims the benefit of, Italian Patent Application No. 102017000098576, filed on Sep. 4, 2017, the contents of which are herein incorporated by reference in their entirety.

TECHNICAL FIELD

The present disclosure relates to a laser therapy apparatus.

The disclosure has specific, but not exclusive, application in the medical sector.

BACKGROUND

Lasers began to be used with success, first in surgery and then for medical use, starting from the 70s in the last century. Also in that decade, the concept of laser therapy was introduced.

Technological developments and the increase in knowledge about the effects of light on organisms have resulted in lasers being currently one of the most widespread forms of physical therapy, because they are not invasive, or minimally invasive, painless, and they have almost no side effects.

Laser light has monochromaticity, coherence and brilliance characteristics that make it unique with respect to any other light source, and which allow to work with great precision on the target tissues.

In surgery, the ability to convey laser light, by way of very thin optic fibers, has made the treatment of several diseases simpler and more efficacious, with great benefits in terms of: reduction of pain, post-operation complications, and risk of infections.

The types of laser used most in medicine and surgery are carbon dioxide lasers ($CO_2$), neodymium YAG lasers (Nd: YAG), and diode lasers.

In particular diode lasers, also known as semiconductor lasers, are the biomedical lasers that are currently most widely used in physiotherapy.

There are many reasons why these lasers are so widespread, the main ones being that they are easy to build, they are small, and they have low costs of maintenance and use. Furthermore, a diode laser is a very versatile system by virtue of the ease with which it is coupled to thin optic fibers, with a diameter of 200-600 µm, which are compatible with the laparoscopic and endoscopic systems currently in use.

The great playback of these laser is also linked to their particular working wavelength, which makes them the most adaptable therapeutic instruments in the entire category.

The radiation of diode lasers that are normally used in laser therapy have a wavelength comprised between 650 nm and 1064 nm.

Scientific research aimed at continuously improving the efficacy of traditional therapeutic lasers has led to the creation of a cutting-edge physical therapy, known as LASERTERAPIA MLS® (Multiwave Locked System).

This therapy is based on lasers with diode sources, the emission characteristics of which have been studied in order to obtain high performance levels in terms of penetration, biological interaction, and safe treatment.

The Multiwave Locked System technology generates a pulse obtained from the combination and synchronization of continuous or "continuous wave" (CW) sources, and pulsed or "pulsed wave" (PW) sources, with different wavelengths. Specifically, the MLS® pulse combines the continuous emission or continuous interrupted (CW-I) emission of an 808 nm diode, which has a certain average power, with the pulsed emission of a 905 nm diode, which can use the high peak power without causing damaging heat effects on the targeted tissues.

The combination of the two wavelengths, 808 nm and 905 nm, allows to take advantage of the combined action of several effects that are triggered by the interaction of these radiations with tissue.

The peculiarity of this pulse lies in the combination and synchronization of the wavelengths, which synergistically boost the therapeutic effects that each of the wavelengths would have if it were used individually.

MLS® laser therapy is manually applied with applicators, which are used at a fixed point or in a scanning manner.

Such known art exhibits drawbacks and aspects that can be improved, however.

To make the system versatile, it is necessary to couple the laser sources with the optic fiber and this needs to be accurate and precise so that the entire device will operate efficiently and reliably, but in the state of the art no systems exist that are capable of conveying the combined and synchronized emission of an 808 nm diode-based continuous source and a 905 nm diode-based source in a single optic fiber.

What is more, the fiber must have a diameter that does not exceed 1500 µm, in order to maintain adequate manageability and flexibility in the manual application terminal.

With regard to coupling optic fiber with pulsed diode sources, such as for example the 905 nm diode, there are some difficulties and limitations:
- the rectangular bundle in output from the chip of the diode laser has a very high divergence,
- the geometry of pulsed diodes, differently from continuous diodes, does not allow to bring the fiber in front of the chip of the source; as a consequence, the laser beam reaches the fiber with an amplitude that is such as to limit the coupling efficiency,
- the greater the power of the pulsed diode, the greater the size of the chip, and as a consequence the size of the output bundle; the use of fibers that are too small for coupling entails considerable losses, the use of optic fibers that are too big facilitates the efficiency for coupling, but it entails a bundle of fibers with a diameter that exceeds the imposed limit of 1500 µm for the final fiber.

Furthermore, no individual pulsed diodes exist with a peak power such that they generate a peak power equal to 1 kW±20%. A similar peak can be reached only through the use of multiple pulsed diodes and a bundle of fibers.

SUMMARY

The aim of the present disclosure is to provide a laser therapy apparatus that is capable of improving the known art in one or more of the above mentioned aspects.

Within this aim, the disclosure provides a laser therapy apparatus that uses the combined and synchronized emission of an 808 nm diode-based continuous source and of 905 nm diode-based pulsed sources, conveying the emission over optic fiber.

The disclosure also provides a laser therapy apparatus that uses the combined and synchronized emission of an 808 nm diode-based continuous source and of 905 nm diode-based pulsed sources, which is capable of generating a peak power of the pulsed component of 1 kW±20% emitted at the handpiece applicator.

The disclosure further provides a laser therapy apparatus that uses the combined and synchronized emission of an 808 nm diode-based continuous source and of 905 nm diode-based pulsed sources, which has a terminal optic fiber connected to the handpiece that can be removed from the machine by way of a connector in order to make it possible, in the event of breakage or malfunction, to ship the spare part to the treatment center without having to ship the entire machine.

The disclosure also provides a laser therapy apparatus that uses the combined and synchronized emission of an 808 nm diode-based continuous source and of 905 nm diode-based pulsed sources, which has a terminal optic fiber, connected to the handpiece, of diameter no greater than 1500 μm in order to ensure adequate manageability and in order to be capable of conveying the laser light on different parts of the body, using the handpiece applicator in a manual scanning manner.

The disclosure further provides a laser therapy apparatus that uses the combined and synchronized emission of an 808 nm diode-based continuous source and of 905 nm diode-based pulsed sources, which enables homogeneity of the two wavelengths, respectively 808 nm and 905 nm, on the surface to be treated.

Furthermore, the present disclosure overcomes the drawbacks of the known art in an alternative manner to any existing solutions.

The disclosure provides a laser therapy apparatus that is highly reliable, easy to implement and at low cost.

This aim and these and other advantages which will become better apparent hereinafter are achieved by providing a laser therapy apparatus according to the disclosure, which comprises a diode-based continuous emission laser source, a diode-based pulsed emission laser source, and a terminal handpiece, characterized in that it comprises a bundle of optic fibers for coupling between individual diodes of said diode based pulsed emission laser source, which is interfaced with a single optic fiber which terminates in said handpiece.

BRIEF DESCRIPTION OF THE DRAWINGS

Further characteristics and advantages of the disclosure will become better apparent from the detailed description that follows of a preferred, but not exclusive, embodiment of the laser therapy apparatus according to the disclosure, which is illustrated for the purposes of non-limiting example in the accompanying drawings wherein.

DETAILED DESCRIPTION OF THE DRAWINGS

Figure 1:
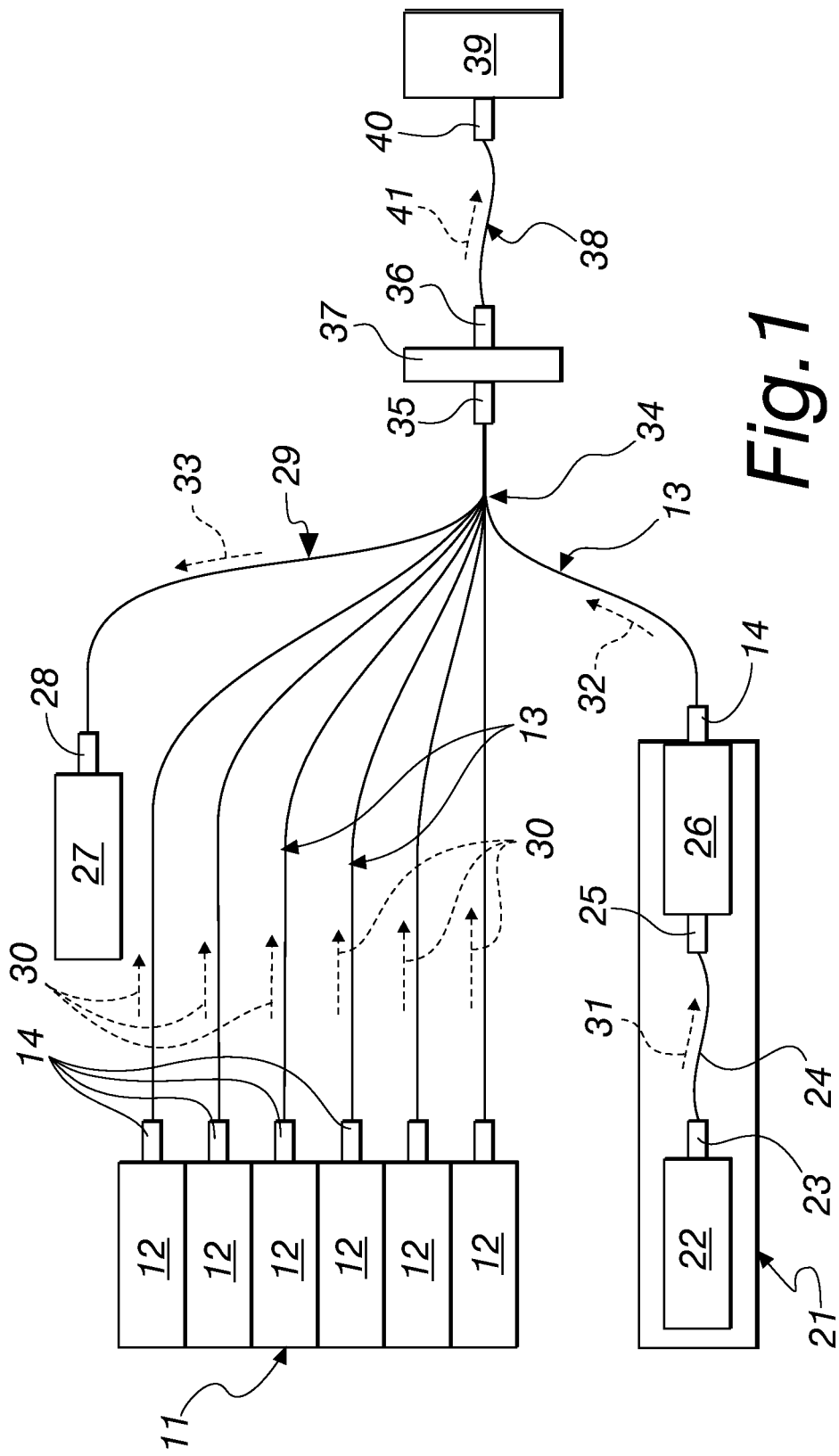
FIG. 1 is a diagram of the operation of the laser therapy apparatus according to the disclosure.

With reference to FIGS. 1-5, the laser therapy apparatus, according to the disclosure, is shown in summary in its operation diagram in FIG. 1 and is generally designated with the reference numeral 10.

The apparatus 10 comprises a pulsed laser source 11. The source 11 is provided with a plurality of conventional diodes 12 with a wavelength of 905 nm. For example, there can be six diodes 12.

In particular, the diode 12 with a wavelength of 905 nm has a peak power of 225 W and a chip with the dimensions 200 μm per 240 μm.

Figure 2:
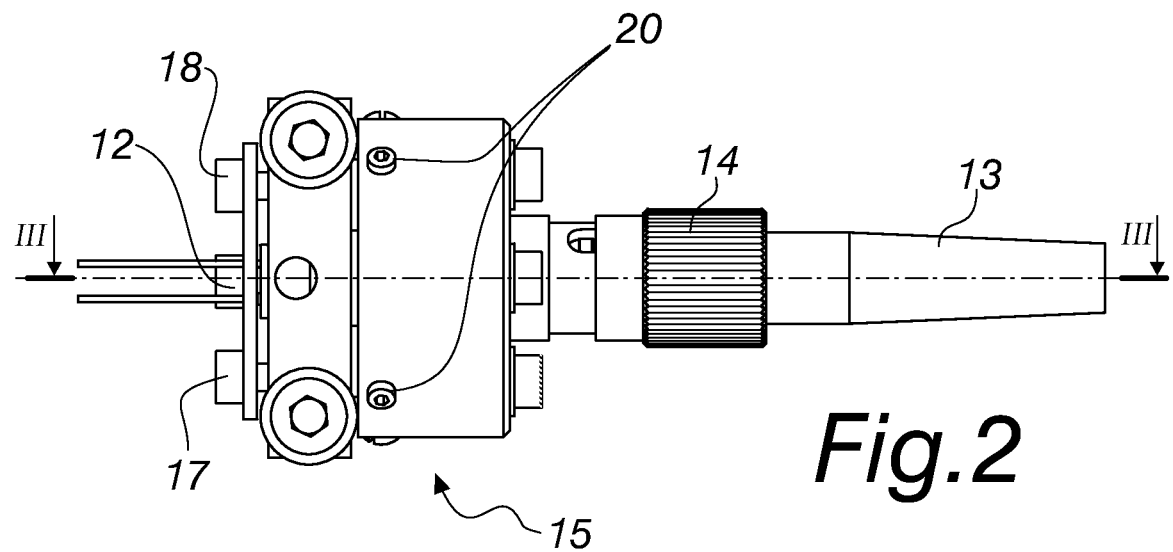
FIG. 2 is a detail of the laser therapy apparatus according to the disclosure.
Figure 3:
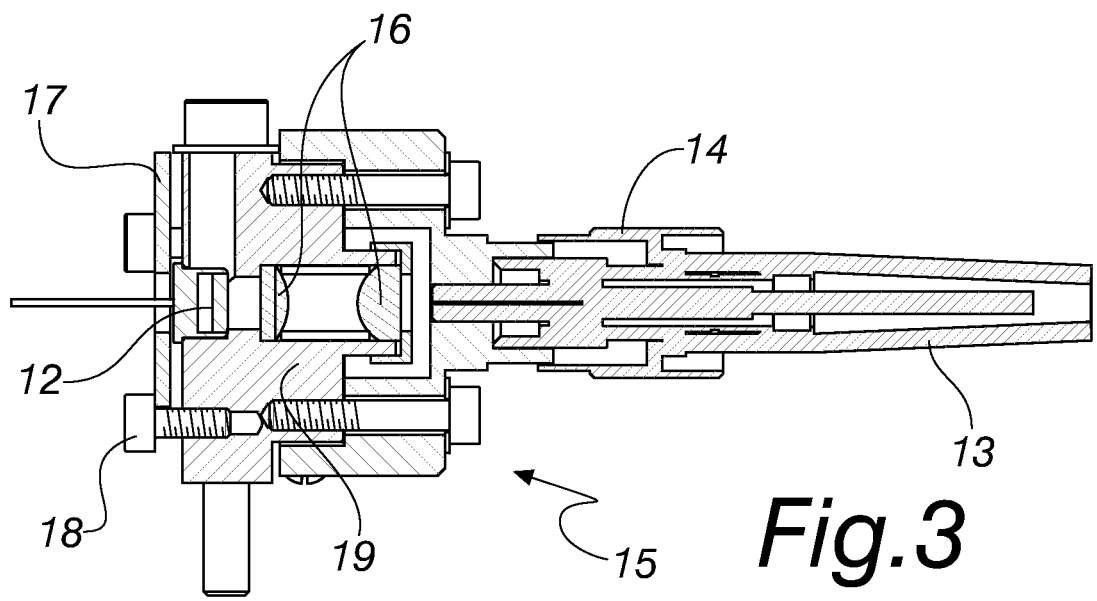
FIG. 3 is a cross-sectional view, taken along the line of the detail in FIG. 2.

The laser beam in output from each diode 12, typically rectangular and diverging, is manipulated by an optical system 15, shown in FIGS. 2 and 3, which makes it possible to efficiently couple the source with an optic fiber 13.

In particular, with reference to FIGS. 2 and 3, the optical system 15 comprises two achromatic doublets 16 which, positioned in front of the diode 12, allow the laser beam to be conveyed with an optic fiber 400 μm in diameter and a numeric aperture NA of 0.48, optimizing the coupling with an efficiency of 74%.

The numeric aperture NA is defined as the non-dimensional parameter that indicates the maximum angle useful to the system for receiving or emitting light.

The diode 12 of the pulsed source is connected to the body 19 of the optical system 15 through a plate 17 which is fixed by way of locking screws 18.

The alignment between the diode 12 and the achromatic doublets 16 is calibrated with a plurality of alignment screws 20.

The presence of the optical system 15 described above allows, in the event of malfunction of or damage to the diode 12, to replace the laser source alone without needing to replace the entire diode/fiber block, with considerable reduction of costs.

Each optical system 15 is coupled to a respective optic fiber 13, by means of a corresponding conventional first FC connector 14.

The optic fiber 13 has a diameter of 400 μm and an NA of 0.48.

The direction of travel of the light is that indicated by the arrows 30.

The electronics and the software of the apparatus enable the synchronized emission of all the diodes 12 at the same time. From this it is possible to obtain, in output, a pulsed emission with peak power equal to 1 kW±20%.

The apparatus 10 also comprises a continuous laser source 21, which has a diode 22 with a wavelength of 808 nm. The diode 22 of the continuous source 21 is coupled to an optic fiber 24 with a diameter of 200 μm by means of a conventional first SMA connector 23.

The optic fiber 24, by means of a conventional second FC connector 25, is coupled to a numerical aperture adapter 26, which is constituted by a conventional optical system.

The numerical aperture adapter 26 allows to convey the laser beam of the 808 nm diode 22 with an angle of divergence equivalent to that of the pulsed 905 nm diode 12. In this manner, at the output of the adapter 26 the beam is prepared to be coupled to the other fibers.

From the adapter 26, by means of a third FC connector 14, the beam is directed to an optic fiber 13 with a diameter of 400 μm and an NA of 0.48.

The direction of travel of the light is that indicated by the arrows 31 and 32.

The optic fibers 13, originating from the pulsed source 11 and from the continuous source 21, are collected in a bundle 34.

The apparatus 10 also comprises a photodiode 27, which is coupled by means of a fourth FC connector 28 to an optic fiber 29.

The optic fiber has a diameter of 200 μm and an NA of 0.37 and terminates in the bundle 34.

The function of the 200 μm fiber 29 is to collect the reflected light, which is produced by every separation surface along the optical path of the laser beam, and to convey it onto the photodiode 27 which is capable of detecting the emission presence. In the first moments of emission, for a very short period of time, the pulsed diodes 12 are made to operate one after the other in succession, the photodiode 27 is therefore capable of verifying the correct operation of the individual pulsed diodes and of diagnosing any malfunctions.

The direction of travel of the light in the fiber 29 is that indicated by the arrow 33.

The fibers 13 and 29 of the bundle 34 are combined in a second SMA connector 35.

The second SMA connector 35 is connected, by means of a coupling plate 37, to a third SMA connector 36, which in turn is connected to a single optic fiber 38 with a diameter of 1500 μm and an NA of 0.37.

In this manner, the bundle 34 of fibers is interfaced with a single, 1500 μm fiber by way of the SMA connectors 35 and 36.

The fiber 38 is connected to a handpiece 39 which is used for the laser therapy, by means of a fourth SMA connector 40.

The direction of travel of the light in the fiber 38 is that indicated by the arrow 41.

Figure 4:
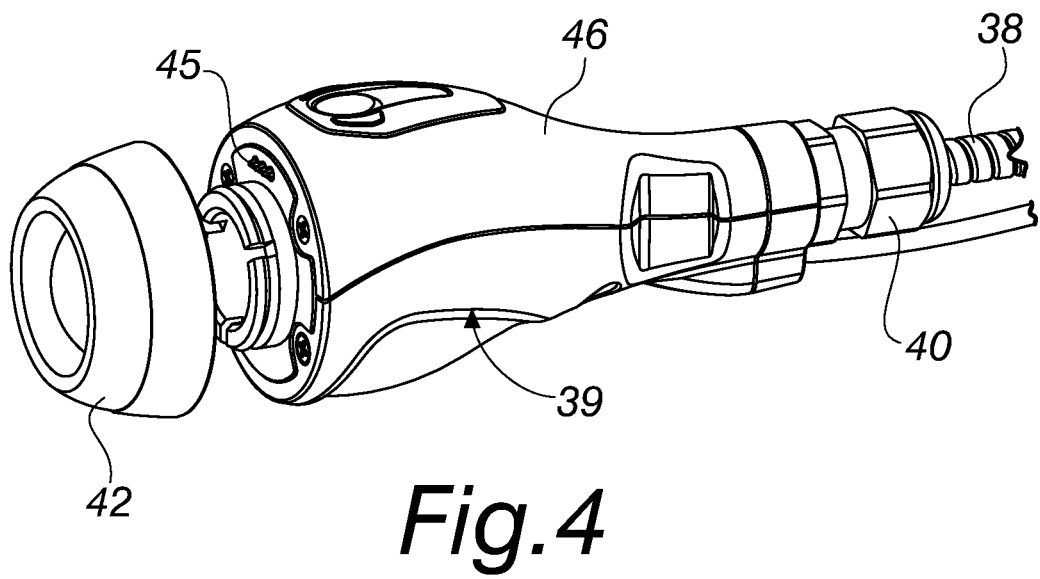
FIG. 4 is a view of a detail of the laser therapy apparatus according to the disclosure.
Figure 5:
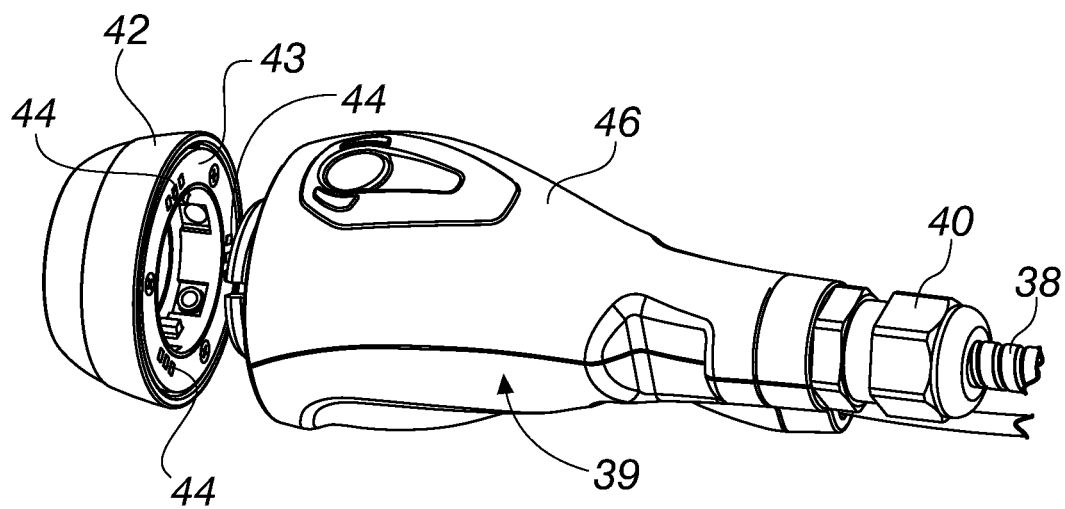
FIG. 5 is another view of the detail in FIG. 4.

In particular, the handpiece 39 is provided with an interchangeable terminal 42, shown in FIGS. 4 and 5, with various different optics so as to have, depending on the application, an output beam of different diameter and divergence.

Each interchangeable terminal 42 is provided with a printed circuit for identification 43, in the section that faces the fixed part 46 with a specific electrical resistance.

On the printed circuit 43 there are three connection elements 44, which are arranged at 120° with respect to each other.

On the fixed part 46 of the handpiece 39 there are electrical contacts 45, on the cross-section facing the printed circuit 43 of the terminal 42, which are adapted for electrical connection therewith, by means of one of the three connection elements 44.

Recognition of the optical terminals 42 occurs by means of electrical contact.

The contacts 45, by means of an internal circuit, are capable of detecting different electric resistors by contact.

When a given optic 42 is attached to the handpiece 39, the system is capable of measuring the electric resistance of that optic 42, and the type of optic used, and set appropriate operating parameters.

The connection system between the handpiece and the optics is designed to avoid rubbing and deterioration of the electrical contacts. Rotation is not permitted between the fixed part and the moveable part, when connected, but there are three connection possibilities 44, which are arranged 120° from each other.

It should be noted that the apparatus according to the disclosure improves the efficiency for coupling between high-power pulsed diodes with a wavelength of 905 nm and optic fiber with respect to the pre-fibered diodes available on the market.

Furthermore it should be noted that the apparatus according to the disclosure allows replacement of the diode, in the event of damage, without the need to replace the entire diode/fiber block, with considerable reduction of costs.

It should also be noted that the apparatus according to the disclosure enables the emission of a pulse at a wavelength of 905 nm with a peak power of 1 kW±20%, conveying it by means of a 1500 μm optic fiber, which is functional and adequately flexible for therapeutic use.

It should be noted that the apparatus according to the disclosure enables the combined and synchronized emission of diode-based continuous wave sources at a wavelength of 808 nm and diode-based pulsed wave sources at a wavelength of 905 nm with a perfect superimposition of the emission components and a homogeneous treatment spot.

Finally it should be noted that the presence of a photodiode allows to verify the emission of the pulsed lasers, identifying any malfunctions.

In practice it has been found that the disclosure fully achieves the intended aims and advantages.

The disclosure thus conceived is susceptible of numerous modifications and variations. Moreover, all the details may be substituted by other, technically equivalent elements.

In practice the materials employed, provided they are compatible with the specific use, and the contingent dimensions and shapes, may be any according to requirements and to the state of the art.

What is claimed is:

1. A laser therapy apparatus comprising: a diode-based continuous emission laser source, a diode-based pulsed emission laser source, and a terminal handpiece, and further comprising a bundle of optic fibers for coupling between a plurality of individual diodes of said diode-based pulsed emission laser source, said bundle of fibers is interfaced with a single optic fiber which terminates in said handpiece, wherein said individual diode of said diode-based continuous emission laser source is coupled to an optic fiber by way of a first SMA connector and wherein said optic fiber, by means of a first FC connector, is coupled to a numerical aperture adapter connected, by way of a second FC connector, to an optic fiber that terminates in said bundle.

2. The laser therapy apparatus according to claim 1, further comprising a photodiode, which is coupled by means of an FC connector to an optic fiber that terminates in said bundle.

3. The laser therapy apparatus according to claim 1, wherein said handpiece has a fixed part and an interchangeable terminal.

4. The laser therapy apparatus according to claim 1, wherein said diode-based pulsed laser source comprises a plurality of said individual diodes with a wavelength of 905 nm.

5. The laser therapy apparatus according to claim 4, wherein said plurality of individual diodes are six in number.

6. The laser therapy apparatus according to claim 2, further comprising an optical system which comprises two achromatic doublets positioned in front of each individual diode.

7. The laser therapy apparatus according to claim 6, further comprising a plurality of screws for alignment between said individual diodes and said achromatic doublets.

8. The laser therapy apparatus according to claim 6, wherein each said optical system is coupled to an optic fiber that terminates in said bundle.

9. The laser therapy apparatus according to claim 1, wherein said diode-based continuous laser source has a wavelength of 808 nm.

10. A laser therapy apparatus comprising: a diode-based continuous emission laser source, a diode-based pulsed emission laser source, a terminal handpiece having a fixed part and an interchangeable terminal, and a bundle of optic fibers for coupling between a plurality of individual diodes of said diode-based pulsed emission laser source, said bundle of fibers is interfaced with a single optic fiber which terminates in said handpiece, wherein said interchangeable terminal is provided with a printed circuit for identification, in a section that faces the fixed part with a specific electrical resistance.

11. The laser therapy apparatus according to claim 10, wherein on said printed circuit there are three connection elements, which are arranged at 120° with respect to each other.

12. The laser therapy apparatus according to claim 10, wherein on said fixed part of the handpiece there are electrical contacts on a section that faces the printed circuit of the terminal.

* * * * *